United States Patent
Salamitou

(10) Patent No.: US 6,956,376 B2
(45) Date of Patent: *Oct. 18, 2005

(54) DEVICES FOR CHARACTERIZING A MULTIPHASE FLUID HAVING A CONTINUOUS CONDUCTIVE PHASE

(75) Inventor: Philippe Salamitou, Mamaroneck, NY (US)

(73) Assignee: Schlumberger Technology Corporation, Sugar Land, TX (US)

( * ) Notice: Subject to any disclaimer, the term of this patent is extended or adjusted under 35 U.S.C. 154(b) by 63 days.

This patent is subject to a terminal disclaimer.

(21) Appl. No.: 10/239,009
(22) PCT Filed: Mar. 12, 2001
(86) PCT No.: PCT/EP01/02762
§ 371 (c)(1), (2), (4) Date: Dec. 17, 2002
(87) PCT Pub. No.: WO01/71327
PCT Pub. Date: Sep. 27, 2001

(65) Prior Publication Data
US 2004/0012395 A1 Jan. 22, 2004

(30) Foreign Application Priority Data
Mar. 22, 2000 (FR) .............................. 00 03629

(51) Int. Cl.[7] ................................................ G01N 27/02
(52) U.S. Cl. ...................................................... 324/444
(58) Field of Search ........................... 324/444, 442; 73/861.04, 861.02, 861.08

(56) References Cited

U.S. PATENT DOCUMENTS 5,883,516 A * 3/1999 Van Steenwyk et al. ..... 324/366

FOREIGN PATENT DOCUMENTS

FR          A 2780499          * 12/1999          ............ G01D/5/24

OTHER PUBLICATIONS

FR 1307879 A (The wayne kerr laboratories LTD.) Feb. 15, 1963 p. 3, left–column, line 3–line 54; Figure 1.*

* cited by examiner

*Primary Examiner*—Anjan Deb
*Assistant Examiner*—Amy He
(74) *Attorney, Agent, or Firm*—Victor H. Segura; Brigitte L. Echols

(57) ABSTRACT

A device for determining the mean resistivity of a multiphase fluid having a continuous conductive phase, includes a pipe segment (4) of insulating material and a oil (6) for generating an electric current in the fluid flowing along the pipe. The device has two measurement electrodes (10, 11) spaced apart in the axial direction of the insulating segment to measure the electrical resistance between said two electrodes, the measurement electrodes being applied to the outside of the wall of the segment to perform measurement by capacitive coupling. The voltage between the measurement electrodes is measured. The device is particularly useful for determining the volume fraction ("holdup") of water in a mixture of water and hydrocarbons.

11 Claims, 1 Drawing Sheet

DEVICES FOR CHARACTERIZING A MULTIPHASE FLUID HAVING A CONTINUOUS CONDUCTIVE PHASE

BACKGROUND OF THE INVENTION

The present invention relates to a device for determining the mean resistivity of a multiphase fluid having a continuous conductive phase, and more particularly it relates to such a device having a segment of insulating pipe and means for generating an electric current in the fluid flowing along said pipe. The invention also relates to a device for determining the volume fraction occupied by a resistive fluid in a multiphase fluid having a continuous conductive phase, and also to a method of determining the mean resistivity of such a fluid.

Document FR-A-2 780 499 discloses devices for characterizing the flow of a multiphase fluid, using capacitive sensors. Such devices serve in particular to determine the dielectric constant of an insulating fluid and to deduce therefrom the volume fractions of the two phases when the fluid is a two-phase fluid. These devices can provide satisfactory results, but cannot be used with a multiphase fluid in which the conductive phase is continuous since the fluid is then no longer insulating. This occurs, for example, in a well for extracting hydrocarbons when the water fraction exceeds a certain value.

Document FR-A-1 307 879 discloses a device for measuring flowing fluids in a pipe having an insulating liner. Current source and measurement electrodes are placed inside the liner in contact with the flowing fluid in order to make the measurements Characterizing devices are also known that comprise a segment of insulating pipe and means for generating an electric current in the fluid flowing in said pipe. These devices thus complement the preceding devices since they apply to multiphase fluids having a continuous conductive phase, i.e. fluids that are not insulating.

The difficulty with the latter devices lies in measuring the potential difference between two points of the fluid to deduce the electrical resistance between said two points, given knowledge of the current. Thereafter, said resistance is used to deduce the mean resistivity given that the shape of the pipe is known.

The present invention seeks to provide means enabling such a measurement to be performed.

More particularly, the invention seeks to provide such means that are insensitive to corrosion and to the surface state of the inside face of the wall of the pipe.

BRIEF SUMMARY OF THE INVENTION

To this end, the invention firstly provides a device for determining the mean resistivity of a multiphase fluid having a continuous conductive phase, the device comprising a pipe segment of insulating material and means for generating an electric current in the fluid flowing along said pipe, the device being characterized by the fact that it comprises two measurement electrodes spaced apart in the axial direction of the insulating segment to measure the electrical resistance between said two electrodes, said measurement electrodes being applied to the outside of the wall of said segment to perform measurement by capacitive coupling, and by the fact that it further comprise measurement means for measuring the voltage between said measurement electrodes.

The measurement can thus be treated as a "4-point" resistance measurement.

This arrangement presents the advantage of not depending on the contact impedance between the fluid and the upstream and downstream metal portions of the pipe. The surface state of the pipe thus has no effect on the measurement.

Furthermore, no measurement electrode comes into contact with the fluid. There is thus no risk of corrosion. This characteristic makes the device of the invention particularly suitable for continuous measurements, particularly downhole. It is thus possible to fit a production tube with measurement segments of the invention at the levels of the fluid inlets, and thus monitor the actual production of each production zone in a hydrocarbon well. The device is also suitable for performing continuous measurements on the surface, in particular at a well head.

In a particular embodiment, said measurement electrodes are annular electrodes placed around insulating pipe segment.

Also in a particular embodiment, provision is made for a guard electrode to surround each of said measurement electrodes.

More particularly, said measurement means for measuring the voltage between said measurement electrodes may be arranged to maintain the voltages of said guard electrodes at the same values as the voltages of the corresponding measurement electrodes.

Said measurement means for measuring the voltage between said measurement electrodes may also be arranged so that the current flowing between the measurement electrodes is small enough to avoid affecting the measured voltage. Thus, the potential difference between the two electrodes is equal to the potential difference between the points in the fluid facing the electrodes.

In this case, said measurement means for measuring the voltage between said measurement electrodes may comprise respective follower amplifiers associated with each of said measurement electrodes, each amplifier having one of its inputs connected to a measurement electrode and its other input connected to the corresponding guard electrode and having its output connected to said guard electrode, said device further comprising means for determining the potential difference between the outputs of the two follower amplifiers. Such a follower amplifier possesses high input impedance which avoids the potential drop due to current passing through the insulation by the capacitive effect. Its output voltage is equal to the input voltage, but current is available at its output. More particularly, each follower amplifier may be connected to the corresponding measurement electrode by the core of a coaxial cable, and to the corresponding guard electrode by the shield of said cable.

In a particular embodiment, said means for generating an electric current in the fluid flowing in said pipe comprise a toroidal emitter coil surrounding said insulating segment and a return electrical conductor interconnecting metal portions of the pipe situated respectively upstream and downstream from the insulating segment. Such a coil has the advantage of not coming into contact with the fluid, and thus of being unaffected by corrosion problems. The emitter coil, connected to an AC voltage generator, generates an electric field in the fluid and thus behaves like a primary winding of a transformer whose secondary winding is constituted by the fluid and the return conductor. This electric field generates the above-specified current, which depends on the resistance of the fluid.

Also in a particular embodiment, the device of the invention comprises a toroidal receiver coil surrounding said insulating segment to form a current measuring system.

Each receiver coil is connected to an electronic circuit having low input impedance. The output from said electronic circuit delivers a signal that is proportional to the current flowing in the fluid. In this case, the device may comprise means for determining the ratio between the output from the voltage-measurement means for measuring the voltage between said measurement electrodes and the output from the current-measuring system. This ratio is proportional to the resistance of the fluid, ignoring contact impedance.

The invention also provides a device for determining the volume fraction (or "holdup") of the conductive fluid in a multiphase fluid having a continuous conductive phase, the device being characterized by the fact that it comprises a device of the type described above to measure the mean resistivity of said multiphase fluid, and means for deducing said volume fraction from said resistivity.

Determining said volume fraction requires not only knowledge of the mean resistivity, but also knowledge of the resistivity of the conductive phase and of the flow conditions. The resistivity of the conductive phase is assumed to be known by other means, and it is shown that various assumptions can be made about the flow conditions.

The invention also provides a method of determining the mean resistivity of a multiphase fluid having a continuous conductive phase, the method being characterized by the fact that it comprises the steps consisting in using capacitive coupling to measure the resistance of the fluid in a pipe segment of insulating material, and in deducing the mean resistivity therefrom.

BRIEF DESCRIPTION OF THE DRAWINGS

There follows a description by way of non-limiting example of a particular embodiment of the invention, given with reference to the accompanying drawing, in which.

DETAILED DESCRIPTION OF THE INVENTION

Figure 1:
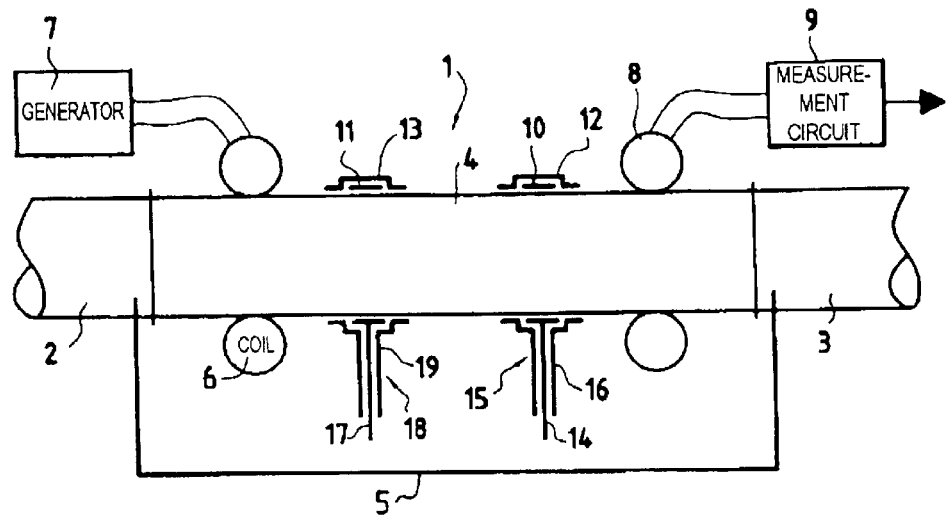
FIG. 1 is an overall view of a device according to one embodiment of the invention.
Figure 2:
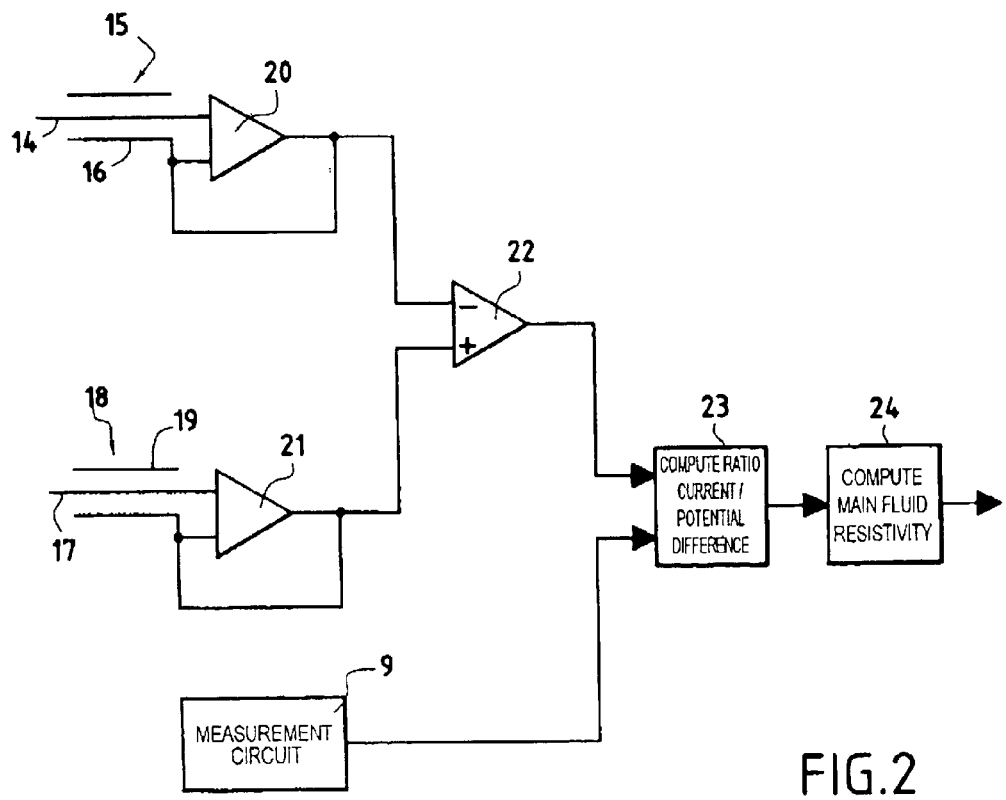
FIG. 2 is an electrical circuit diagram.

FIG. 1 shows a pipe 1 in which a two-phase fluid flows, in this case a mixture of water and of hydrocarbons. The water fraction is large enough to ensure that the aqueous phase is continuous, such that the mixture is electrically conductive. The pipe 1 can form part of an outlet from a hydrocarbon well, for example production tubing or a surface outlet pipe. Also, it can form part of the completion downhole or be connected to an outlet pipe of a pump (for example an electric submersible pump or "ESP"), or any other conduit typically found in a hydrocarbon-producing well.

The pipe 1 is constituted by an upstream segment 2 and a downstream segment 3 that are both made of metal, together with a measurement segment 4 of a material that is electrically non-conductive. An electrical conductor 5 interconnects the conductive segments 2 and 3 so as to form an electric circuit that is closed by means of the fluid flowing along the pipe.

A toroidal emitter coil 6 is disposed around the pipe 1 inside the current loop defined by the conductor 5, e.g. in the upstream portion of the measurement segment 4 as shown herein. The coil 6 is powered by a generator 7 for generating an alternating voltage. It thus generates an alternating electric field in the fluid which in turn generates an alternating current in the fluid and in the conductor 5.

A toroidal receiver coil 8 is disposed around the pipe 1, likewise within the current loop defined by the conductor 5, e.g. in the downstream portion of the measurement segment 4. The coil 8 is connected to a measurement circuit 9 having low input impedance. The current in the fluid induces a current in the coil 8 such that the output signal from the measurement circuit 9 is proportional to the current in the fluid.

Two annular measurement electrodes 10 and 11 are disposed on the outside surface of the pipe segment 4. They are covered by two respective guard electrodes 12 and 13.

The output from the measurement electrode 10 takes place via the core conductor 14 of a coaxial cable 15 which passes through a hole in the guard electrode 12. The shield 16 of the coaxial cable 15 is connected to said electrode 12.

Similarly, the output from the measurement electrode 11 is taken via the core conductor 17 of a coaxial cable 18 which passes through a hole in the guard electrode 13. The shield 19 of the coaxial cable 18 is connected to said electrode 13.

The core 14 of the cable 15 is connected at one input to a follower amplifier 20 whose other input and whose output are connected to the shield 16. Similarly, the core 17 of the cable 18 is connected to one input of a follower amplifier 21 whose other input and whose output are connected to the shield 19.

Thus, the electrodes in each of the pairs 10 & 12 and 11 & 13 are maintained at the same potential as each other and a very small current flows along the conductors 14 and 17, such that each of the electrodes 10 and 11 is at the same potential as the fluid facing it on the other side of the wall of the pipe segment 4.

The outputs from the amplifiers 20 and 21 are applied respectively to the inverting and to the non-inverting inputs (− and +) of a differential amplifier 22. The output from the amplifier 22 is thus representative of the potential difference in the fluid between the planes of the electrodes 10 and 11.

The output from the measurement circuit 9, i.e. the current in the fluid, and the output from the amplifier 22, i.e. the above-mentioned potential difference, are input to circuit 23 which determines the ratio of these two quantities. The output from the circuit 23 is thus representative of the resistance of the fluid between the planes of the electrodes 10 and 12.

Given knowledge of the cross-section of the segment 4 and the axial distance between the electrodes 10 and 12, it is possible in a circuit 24 to deduce the mean resistivity of the fluid.

From the above, and by using appropriate computation means, it is thus possible to deduce the water volume fraction or "holdup" of the two-phase mixture, assuming that the resistivity of the water is known, and making assumptions about the flow conditions of the fluid.

For a flow that is well stratified, the water and the hydrocarbons flow along the pipe in the form of two separate layers. Under such circumstances:

$$R = \rho_W \frac{L}{S_W}$$

where $\rho_w$ is the resistivity of the water, $S_w$ is the cross-section of the water layer, and L is the distance between the measurement electrodes.

The volume fraction or "holdup" of the water $H_w$ is then:

$$H_w = \frac{S_w}{S} = \frac{\rho_w L}{RS}$$

where S is the total cross-section of the pipe.

Conversely, for a flow that is entirely uniform, the resistivity of the mixture $\rho_{mix}$ is given by:

$$R = \rho_{mix} \frac{L}{S}$$

The water volume fraction $H_w$ is then deduced from the "Ramu Rao" formula:

$$\rho_{mix} = \rho_w \frac{3 - H_w}{2H_w} \quad 3 - H_w$$

The output from the devices described above can be used to characterise the flow from a hydrocarbon well. This can be the total output of the well or the flow in a particular section of the well. The invention finds particular use in conjunction with downhole pumps used in wells with low natural flows.

What is claimed is:

1. A device for determining the mean resistivity of a multiphase fluid having a continuous conductive phase, the device comprising:
   a pipe segment of insulating material including two measurement electrodes spaced apart in an axial direction of the insulating segment to measure the voltage between said measurement electrodes, the measurement electrodes being applied to an outside of the wall of the segment so as to perform measurements by capacitive coupling;
   means for generating an electric current in the fluid flowing along said pipe; and
   means for measuring the current in the fluid.

2. The device of claim 1, wherein the measurement electrodes are annular electrodes placed around the insulating pipe segment.

3. The device of claim 1, further comprising a guard electrode surrounding each of the measurement electrodes.

4. The device of claim 3, wherein the measurement circuit maintains the voltages of the guard electrodes at the same values as that of the corresponding measurement electrodes while measuring the voltage between the measurement electrodes.

5. The device of claim 4, wherein the measurement circuit comprises respective follower amplifiers associated with each measurement electrode, each amplifier having one of its inputs connected to a measurement electrode and its other input connected to a corresponding guard electrode and having its output connected to the guard electrode, the measurement circuit determining the potential difference between the outputs of the two amplifiers.

6. The device of claim 5, wherein each follower amplifier is connected to the corresponding measurement electrode by a core of a coaxial cable, and to the corresponding guard electrode by a shield of the coaxial cable.

7. The device of claim 1, wherein the measurement circuit is arranged so that the current flowing between the measurement electrodes is sufficiently small that there is substantially no effect on the voltage measured between the measurement electrodes.

8. The device of claim 1, wherein the means for generating an electric current in the fluid comprise a toroidal emitter coil surrounding the insulating segment and a return electrical conductor interconnecting metal portions of the pipe situated respectively upstream and downstream from the insulating segment.

9. The device of claim 1, further comprising a toroidal receiver coil surrounding the insulating segment for measuring the current.

10. The device of claim 9, further comprising means for determining the ratio between the output of the voltage measurement and the output of the current measurement.

11. The device of claim 1, further comprising means for determining the volume fraction of conductive fluid in a multiphase fluid having a continuous conductive phase from a measurement of the mean resistivity of the multiphase fluid.

* * * * *